US006968229B2

(12) United States Patent
Siemons (10) Patent No.: US 6,968,229 B2
(45) Date of Patent: Nov. 22, 2005

(54) APEX LOCATING SYSTEM

(75) Inventor: Alexander H. Siemons, Sierra Madre, CA (US)

(73) Assignee: Ormco Corporation, Orange, CA (US)

( * ) Notice: Subject to any disclaimer, the term of this patent is extended or adjusted under 35 U.S.C. 154(b) by 124 days.

(21) Appl. No.: 10/430,965

(22) Filed: May 6, 2003

(65) Prior Publication Data

US 2004/0225234 A1 Nov. 11, 2004

(51) Int. Cl.[7] .............................. A61B 5/05; A61B 5/103
(52) U.S. Cl. ....................... 600/547; 600/590; 433/27; 33/513
(58) Field of Search .............................. 600/547, 590; 433/27, 28, 32, 72, 75, 215; 33/513, 514

(56) References Cited

U.S. PATENT DOCUMENTS

| | | | |
|---|---|---|---|
| 3,901,216 A | 8/1975 | Felger | 128/2.1 |
| 3,916,529 A | 11/1975 | Mousseau | 33/174 |
| 3,993,044 A | 11/1976 | McGuffin | 128/2 |
| 4,193,408 A | 3/1980 | Fujino | 128/734 |
| 4,243,388 A | 1/1981 | Arai | 433/27 |
| 4,353,693 A | 10/1982 | Dery et al. | 433/27 |
| 4,447,206 A | 5/1984 | Ushiyama | 433/27 |
| 4,526,179 A | 7/1985 | Salesky | 128/776 |
| 5,017,134 A | 5/1991 | Saito et al. | 433/72 |
| 5,049,069 A | 9/1991 | Salesky | 433/27 |
| 5,080,586 A | 1/1992 | Kawai | 433/32 |
| 5,096,419 A | 3/1992 | Kobayashi et al. | 433/72 |
| 5,112,224 A | 5/1992 | Shirota | 433/27 |
| 5,211,556 A | 5/1993 | Kobayashi et al. | 433/72 |
| 5,295,833 A | 3/1994 | Chihiro et al. | 433/224 |
| 5,759,159 A | 6/1998 | Masreliez | 600/547 |
| 5,902,105 A * | 5/1999 | Uejima et al. | 433/27 |
| 6,059,569 A | 5/2000 | Otsuka | 433/72 |
| 6,221,031 B1 | 4/2001 | Heraud | 600/590 |
| 6,845,265 B2 * | 1/2005 | Thacker | 600/547 |

* cited by examiner

*Primary Examiner*—Peter Nerbun
(74) *Attorney, Agent, or Firm*—Wood, Herron & Evans, L.L.P.

(57) ABSTRACT

A method, apparatus and program product correlates measured endodontic signals to stored distance values indicative of probe position within a root canal. An appropriate distance value is retrieved from a memory having a plurality of electrical signal measurements and other information stored in associative relationship with respective distance values.

20 Claims, 4 Drawing Sheets

| CAPATICANCE (FARADS) | RESISTANCE (OHMS) | DISTANCE (UNITS) |
|---|---|---|
| 0.004 | 3600 | 2.0 |
| 0.004 | 3700 | 1.9 |
| 0.004 | 3800 | 1.9 |
| 0.004 | 3900 | 1.9 |
| 0.004 | 4000 | 1.9 |
| 0.004 | 4100 | 1.8 |
| 0.004 | 4200 | 1.8 |
| 0.004 | 4300 | 1.7 |
| 0.004 | 4400 | 1.7 |
| 0.004 | 4500 | 1.7 |
| 0.004 | 4600 | 1.5 |
| 0.004 | 4700 | 1.5 |
| 0.004 | 4800 | 1.4 |
| 0.004 | 4900 | 1.4 |
| 0.004 | 5000 | 1.3 |
| 0.004 | 5100 | 1.2 |
| 0.004 | 5200 | 1.2 |
| 0.004 | 5300 | 1.0 |
| 0.004 | 5400 | 0.9 |
| 0.004 | 5500 | 0.9 |

APEX LOCATING SYSTEM

FIELD OF THE INVENTION

The present invention relates generally to endodontic procedures, and more particularly, to determining the depth of a root canal.

BACKGROUND OF THE INVENTION

The progression of tooth decay often necessitates excavation of pulp from the root canal of the unhealthy tooth. Such removal is conventionally accomplished by mechanically excavating and enlarging the size of the root canal with a reamer, then sterilizing and filling it with suitable bonding material. While pulp is removed, care must be taken to avoid encroaching on healthy tissues and excessive removal of tooth structure. In the detail oriented, high wear and nerve ridden canal environment, even a small amount of imprecision can translate into over penetration beyond the apical foramen, periodontal membrane. Such over penetration can cause contamination and damage to apical and other tissues, in addition to premature decomposition and patient discomfort. Conversely, an inadequate amount of penetration may cause infectious tissues to remain. Precise knowledge of the depth of the canal can help avoid such incidents.

The practice of locating the apex, or most bottom portion of a root canal, is conventionally accomplished via measurement of electronic signals that permeate the canal region. Conventionally, an endodontist inserts a first electrode into the root canal and contacts a second electrode to the gum or other tissues proximate the root of the tooth. One of the electrodes emits an electronic signal that is received by the second electrode. Variations on this general principle include simultaneous generation of multiple signals having different frequencies.

Electrophysiological studies show that the circuit between the measuring electrode and the oral electrode approximates an equivalent circuit comprised of a resistor and a capacitor connected in parallel. The magnitude of the detected resistance or impedance will vary as the tip of the inserted electrode approaches the apical position. As such, detected impedance, for instance, can be used to determine whether the leading edge of the measuring electrode has arrived at the apical position.

Prior art systems rely on algorithms to marry a ratio or other value derived from the measured impedance or resistance to an apical distance. For instance, many conventional processors use measured impedance to calculate electrode distance as a function of one or more preprogrammed equations. Processors typically execute an appropriate algorithm at periodic intervals to update calculated distances, which are reported to the endodontist.

Despite advances in generating, detecting and processing signals, known apex locating systems and practices remain imprecise. Some such imprecision is attributable to the mathematical limitations inherent to these techniques and associated algorithms. The equations employed by conventional apex finding techniques merely approximate the relationship between the electrode distance and the measured resistance or impedance. While some such algorithms achieve some degree of sophistication, they fail to account for subtle tissue characteristics and environmental variability. Thus, prior art systems remain handicapped in determining apical distance in the variety of conditions that exist.

Consequently, known systems exhibit some level of imprecision and the above discussed risk of over/under root penetration and filling.

Environmental factors affecting a measurement process can further frustrate conventional root canal measuring devices. For instance, resistance measurements are often artificially decreased and otherwise corrupted in the presence of conductive medical liquids, water and blood in the root canal. Output of prior art systems may also be affected unfavorably by the respective sizes of the apical foramen and the measuring electrode, as well as apex morphology and abnormality. These environmental factors introduce an additional, nonlinear variable that can elude conventional algorithms. Thus, the calculated output of the prior art apex locating systems may be compromised and prone to error, often accompanied with the above discussed unfortunate results.

Developing and executing the algorithms of prior art systems can further require large amounts of processing and manpower, as well as other programming resources, to develop and improve upon equations that nonetheless remain fundamentally flawed. Consequently, and for in part the above delineated reasons, there exists a need for an improved manner of determining the depth of a root canal.

SUMMARY OF THE INVENTION

The present invention provides an improved apparatus, method and program product for determining the length of a tooth cavity, thereby enhancing the efficiency and effectiveness of root canal procedures. A signal generated as a function of a probe's location within the tooth cavity is measured by a detection circuit. The measured electrical signal is correlated to a stored distance value. The distance value may be one of a plurality of distance values that are likewise stored in the memory. In this manner, the determined distance value may be output to a display in order to apprize a user of probe position.

Data used to populate the memory may be compiled from clinical studies or other established sources, to include data derived from known mathematical functions. Such resources may precisely reflect actual distances measured in connection with electrical measurements recorded under controlled or otherwise known conditions. As such, the memory may include multiple data sets, as well as abnormal responses determined from clinical data. In any case, the availability of such data represents a marked advantage over prior art applications, which merely approximate canal lengths by limiting analysis to general trends at the expense of more subtle or mathematically anomalous solutions.

The independence of the tabled data of the present invention from the algorithms required by the prior art allows for the inclusion of data that is uniquely tailored to an application. Thus, the data recalled from memory and processed in conjunction with the electrical measurement may include statistics beyond the scope of the algorithms of prior art systems. For example, the present invention may account for apex abnormalities, probe size and material considerations, as well as anticipated electromagnetic interference. Still other exemplary data sources may include a hybrid source, such as clinical data processed to generate a regression equation used, in turn, to generate the data stored in memory. As such a suitable regression equation may include any program configured to processes data to generate a surface curve or any other storable output.

Another embodiment that is consistent with the principles of the present invention may selectively and/or conjunctively process any one of a resistance, capacitance and impedance measurement. Such versatility and data integrity translates into more useful outputs. Moreover, features of the present invention further mitigate concerns regarding fluid conductivity (wet/dry conditions) in the tooth cavity, size aberrations, and other environmental conditions that are already accounted for in the stored data. Furthermore, the stored data may be readily updated and augmented to account for patient conditions such as age, sex, radial lucency, as well as other specific health and equipment conditions. Such modifications may, in some instances, be initiated automatically or manually in realtime. One of skill in the art will appreciate that embodiments that are consistent with the invention may include multiple, different data sets for use in the same or different applications.

The digital storage of the values and measurements within the memory further makes the data easy to access and update, allowing for efficient processing times. For instance, distance values established for a particular individual, or type of individual, may be entered by hand or downloaded from a file as desired. Embodiments of the present invention may further augment and complement existing apex locating hardware.

By virtue of the foregoing there is provided an improved apex locating mechanism that addresses shortcomings of known systems. These and other objects and advantages of the present invention shall be made apparent in the accompanying drawings and the description thereof.

BRIEF DESCRIPTION OF THE DRAWINGS

The accompanying drawings, which are incorporated in and constitute a part of this specification, illustrate an embodiment of the invention and, together with a general description of the invention given above, and the detailed description of the embodiment given below, serve to explain the principles of the invention.

DETAILED DESCRIPTION OF THE PREFERRED EMBODIMENTS

Figure 1:
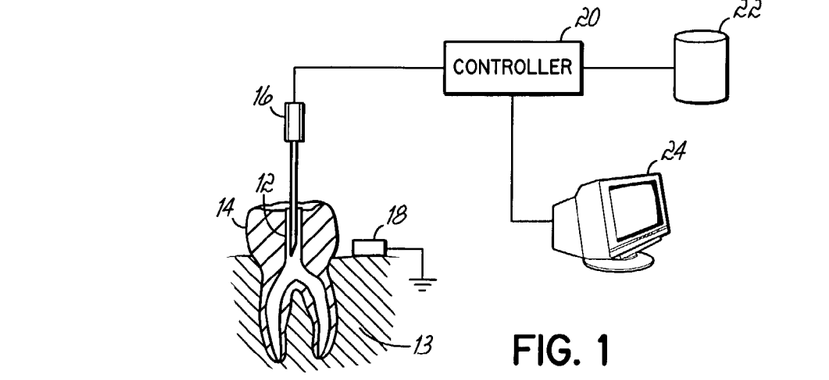
FIG. 1 is a block diagram of a one embodiment consistent with the principles of the present invention.

Referring generally to FIG. 1, there is shown an improved endodontic system 10 configured to more accurately determine the length of a root canal 12 of a patient's tooth 14. The system 10 includes a probe 16 that may generate and/or receive one or more signals from within the root canal 12. The signal(s) may be detected and correlated to a distance value stored within a database. The distance value may be retrieved from the database and ultimately output to a user display 24.

A probe 16 having application within one embodiment of the present invention may include any device that can generate, receive and/or reflect an electronic signal. While such a probe 16 may comprise a thin metal wire, a more typical probe 16 that is consistent the present invention may take a form that provides additional functionality, such as file, rasp or drill bit. Such probe features may serve a dual purpose of cleaning, enlarging or otherwise modifying the inner surface of the root canal 12, while simultaneously enabling apex location. Where desired, a suitable probe 16 may be tapered at one end to facilitate insertion into the root canal 12. A probe 16 of one embodiment may include an attached transmitter configured to generate the signal. An exemplary probe 16 may additionally or alternatively be configured with a receiver for detecting signals reflected or transmitted from one more additional sources.

While metal or laminate based probes may have particular utility in the context of certain applications consistent with the present invention, a suitable probe 16 in another embodiment of the present invention may comprise electromagnetic energy. Electromagnetic waves may include radio or laser energy directed to propagate throughout the root canal 12 and be received by a receiver. Thus, "insertion" of the probe 16 into the root canal 12 may comprise the propagation of electromagnetic radiation, for example.

The probe 16 may be in electronic communication with an electrode 18 or other contact positioned along the tissues of a patient's mouth. For instance, an electrode may attach to the gum of a patient proximate the root of the tooth 14, or clip onto their lip. A suitable electrode 18 of one embodiment may be configured to reflect or receive at least a portion the signal transmitted from the probe 16. For instance, the electrode 18 may be positioned such that it reflects a portion of the signal back to a signal receiver component of the probe 16. As such, the electrode 18 may be grounded. The electrode 18 of another embodiment may be alternatively configured to transmit and/or receive signals that are, in turn, reflected or received by the probe 16. The electrode 18 typically forms a circuit that also comprises patient tissue/ligament 13 and the probe 16.

While a tooth 14 is the typical recipient of a probe 16 according with the invention, one of skill in the art should recognize that the principles of the present invention may apply equally to other tissues of the body, to include ligament, muscle, tendon and cartilage, for instance. Moreover, application of the present invention may extend to processes involving laterally oriented tooth cavities, and it thus not limited to the specific apical orientations and applications included in the specification for explanatory purposes. For this reason, "canal" and "cavity" are used interchangeably throughout the specification. One of skill in the art will further appreciate that the methods and system 10 of the present invention may be used to locate any desired position along the length or width of a canal 12, to include locations just short of the apex, such as by the apical constriction.

A signal for purposes of this specification may include one or more electromagnetic emissions that may vary in frequency, duration, amplitude, as well as analog/digital and modulation. Thus, the signal transmitted from the probe 16 and/or electrode 18 may comprise two or more alternating current (AC) waveforms. Varying frequencies of the respective signals may superimpose, or overlap, as should be appreciated by one of familiarity in the art. The signal may be continuously and/or regularly generated, or may be prompted by a detected incident, such as an instruction from the controller 20 or other input source.

The signal may convey one or more electrical measurements. An exemplary electrical measurement may correspond to a capacitance, a resistance and/or an impedance component of the above discussed equivalent circuit. Capacitance is defined for the purposes of one embodiment of the present invention as energy stored in an electrostatic field, which measured in farads. Resistance concerns current losses and has units measurable in ohms. Impedance may be characterized as resistance varying as a function of time in an analog environment. As is known, measured resistance generally decreases as the distance between the probe 16 and the apex diminishes, and may vary according to capacitance. Such trends are generally present in the three-axis graph of FIG. 2.

Figure 2:
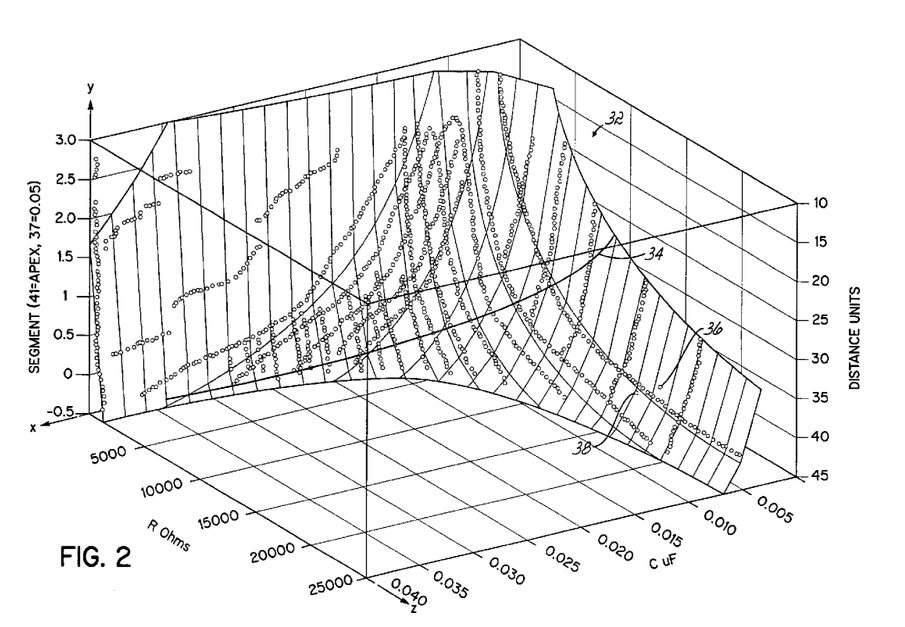
FIG. 2 is a three dimensional graph modeling a surface generated using data suited for use within the system of FIG. 1.

The data populating the graph of FIG. 2 is representative of actual, clinically verified probe distances recorded in relation to actual measured signals. Thus, the exemplary graph plots compiled resistance and capacitance data points as a function of confirmed probe position. As such, the clinical data used to populate the chart of FIG. 2 includes some measurements that defy the above discussed general trends. While such deviation remains unaddressed by conventional processes, such data may have particular application within embodiments of the present invention. Namely, actual data, like that used in conjunction with FIG. 2, may be stored within memory as a resource against which the controller 20 may correlate measured signals.

Data used to populate the memory, like that relied upon to plot the distances and actual electrical measurements of the graph of FIG. 2, may be compiled from clinical studies or other established sources, to include data derived from known mathematical functions. Such resources, as implied above, may precisely reflect actual distances detected relative to sensed electrical measurements under controlled or otherwise known conditions. As developed in the paragraphs that follow, the data maintained within memory may embody actual, verified distances, as well as established estimates, or data from any combination of sources suited to the specific needs of an apex locating operation.

In any case, the availability of actual data represents a marked advantage over prior art applications, which merely approximate canal lengths by focusing, and thereby limiting, analysis to general trends at the expense of more subtle or mathematically anomalous accuracy. Thus, the data recalled by an embodiment of the present invention may account for statistics beyond the scope of the algorithms of prior art systems. Such accuracy translates into more useful outputs.

While data downloaded from a clinical source may present particular advantages in certain contexts, one of skill in the art will also appreciate that useful data of another embodiment consistent with the present invention may include data that has been mathematically generated. Such data may be augmented where desired with additional data to account for known deviations from the algorithmic model. Thus, embodiments of the present invention may avail themselves of those aspects of prior art calculations that retain some benefit, while augmenting results where desired with clinical data.

Turning more particularly to FIG. 2, the graph 32 models resistance and capacitance curves plotted along the x- and z-axes, respectively. Values indicative of probe 16 distance from the apex 15 are plotted along the y-axis in distance units. One of skill in the art should appreciate that such distance units may comprise, or be readily converted into, conventional metric or English units of measurement.

As is shown in FIG. 2, the value of resistance generally decreases as the probe 16 nears the apex 15. This trend is illustrated by phantom line 34. Notably, the plotted data departs from the above trend on numerous occasions, including points 36 and 38 of FIG. 2. As is known in the art, variance from the trends (and the mathematically computed data of the prior art) is a statistically frequent occurrence. Such an occurrence may be attributable to any combination of factors, including fluid conductivities, tissue densities, patient health conditions, power levels, receiver sensitivities, among others.

As discussed above, prior art applications largely ignore such deviations, often compromising an endodontic procedure. Conventional applications suffer because known mathematical functions do not precisely predict or duplicate actual data. In contrast, program code of embodiments of the present invention capitalizes on such data to avoid inaccuracies that are tolerated by prior art applications. In so doing, features of the invention may escape incidents of over/under penetration, damage to healthy tissues, incomplete instrumentation/filling and patient pain that routinely plagues conventional efforts. This feature further obviates investment of vast amounts of processing and manpower, as well as other programming resources conventionally required to develop and improve upon equations that remain fundamentally flawed.

One of skill in the art will appreciate that the level of detail shown in the exemplary chart of FIG. 2 may be expanded to include greater or less granularity according to system specifications. For instance, data supporting another model having application within an embodiment of the present invention may include additional axes and mathematically determined dimensions. For example, surfaces of a mathematical model that accords with the principles of the present invention may include five dimensions or more of correlated data, which may be stored within one or more lookup tables. Other data sources may selectively focus areas of greater detail inline with critical system requirements. Such selective granularity may be instituted for clinical, processing or memory considerations.

The signal conveying the electrical measurement, which may include a detected capacitance, impedance or resistance level, may be formatted at the controller 20, probe 16 or electrode 18 according to processing or transmission protocol of the system 10. Such provision may facilitate speedy correlation of the electrical measurement to an appropriate distance value. As discussed below in greater detail, the distance value may be representative of the position of the probe 16 relative to the apical foreman, or some other appropriate reference point within the canal 12.

Communication of the signal from the probe 16 or electrode 18 to the controller 20 may be accomplished via a cable coupling. Suitable communication may be wireless where desired, such as is possible through radio waves or laser. Where desired, the controller 20 may include an analog to digital converter for sampling the waveform and transforming to a digital format for processing.

In one respect, the controller 20 functions to marry the communicated signal with a tabled distance value that is indicative of probe position within the root canal 12. To this end, a controller 20 for purposes of this invention may include any device having processing capability that is configured to receive and send a signal. Such devices include microchips, computers and networks of computers. Thus, a controller 20 for purposes of an embodiment of the present invention may include multiple controllers located near or remote the patient. To this end, one skilled in the art should appreciate that the controller 20 may include an interface (not shown) with one or more networks (e.g., a LAN, a WAN, a wireless network, and/or the Internet, among others) to permit the communication of information with other controllers coupled to the network.

Thus, various applications, components, programs, objects, modules, etc. may also execute on one or more processors in another controller coupled to the controller 20 via a network. One of skill in the art will recognize that the processing power of the controller 20 may be augmented or otherwise tailored to the requirements and budgets of the individual applications, and may be optimized for superior processing advantages. Where advantageous for space or other considerations, the controller 20 may be manufactured integrally with the probe 16.

The controller 20 typically has access to a memory 22. While the memory may be integral with the controller 20, suitable memory may be located throughout an apex locating system 10, to include some storage that is remote from the controller 20. The memory, which may comprise a database, combination lookup table, and/or RAM, for instance, may generally store signal measurements in an associative relationship with distance values.

Figure 3:
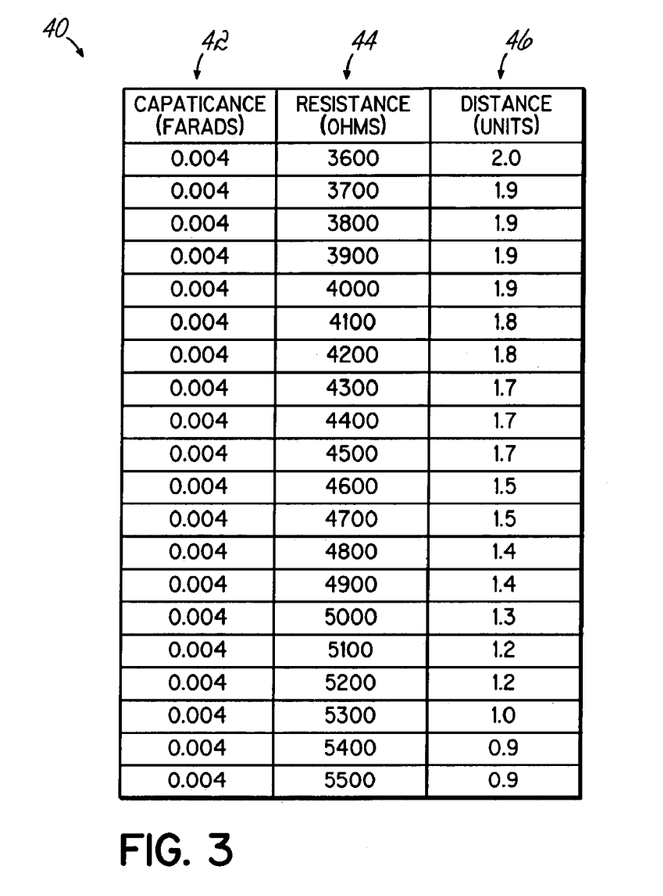
FIG. 3 is an exemplary table containing distance values as correlated to electrical measurements suited to populate the database of FIG. 1.

The exemplary lookup table 40 of FIG. 3 shows one embodiment of memory that is consistent with the principles of the present invention. The table 40 features three columns 42–46, each column 42–46 containing data stored in an associative relationship. The table 40, in one respect, presents a versatile platform from which distance values 46 can be readily determined and output to a user based on input from correlated capacitance and resistance measurements 42, 44. Where so configured, one or much such lookup tables may be accessed by the controller 20 in order to correlate the electrical measurements to an accurate distance value.

Exemplary distance values, which may be indicative of probe 16 distance from the apex, may comprise conventional metric or English units of measurement, where preferred. As discussed herein, it should be appreciated that other columns embodying additional criteria may be included within tables or other memory in accordance with the principles of the present invention. Thus, the invention should not be construed as being limited by the exemplary scope of the illustrated lookup table 40 of FIG. 3.

Figure 4:
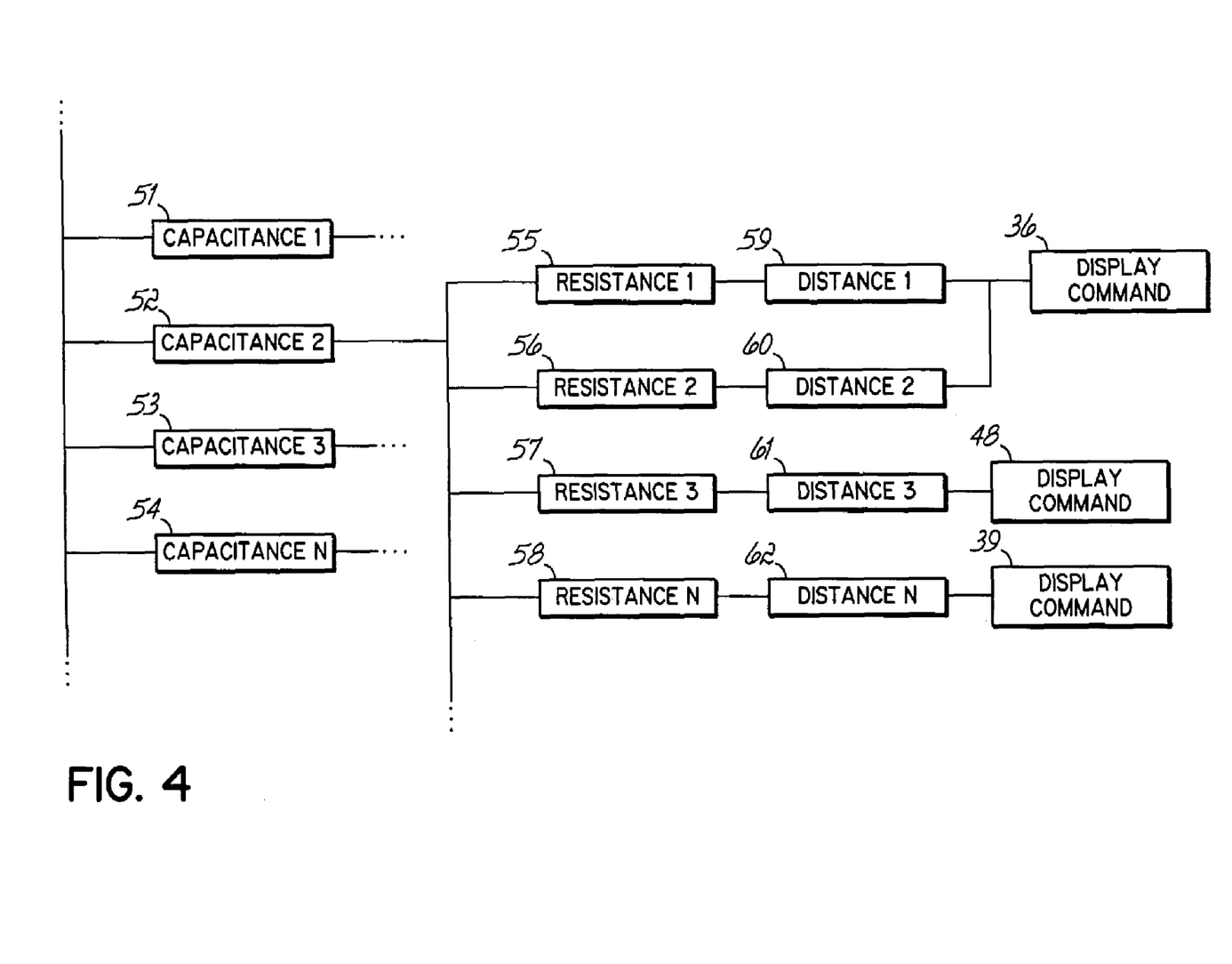
FIG. 4 is a database schematic having application within the block diagram of FIG. 1.
Figure 5:
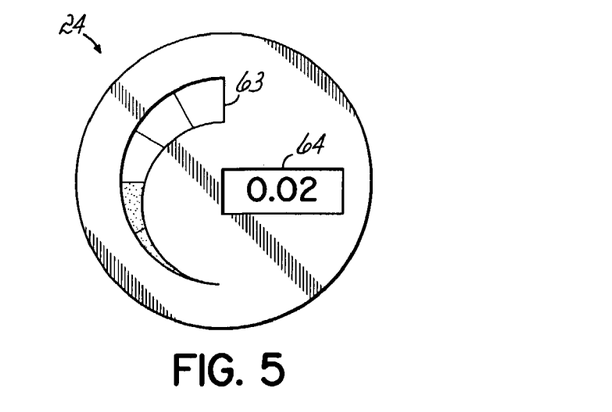
FIG. 5 shows a display having application within the system of FIG. 1.

One of skill in the art should further recognize that there are many number of different ways to store endodontic data in accordance with the present invention. Nevertheless, the database schematic 50 of FIG. 4 shows an exemplary logical structure that may be particularly suited to store and recall distance values in relation to electrical measurements in accordance with an embodiment of the present invention. As discussed herein, such a database may be stored in physical memory located throughout the system 10, either or both local and remote to the controller 20.

The database schematic 50 of FIG. 4, in one respect, logically links one or more fields containing electrical measurements 51–58 to other, appropriate fields that contain distance values 59–62. The logical connectivity within the exemplary schematic 50 accounts for different system operating parameters, such as capacitance 51–54 and detected resistance 55–58 of received signals. While these measurements 51–58 do affect the output 48 under certain conditions, one of skill in the art should appreciate that their inclusion within FIG. 4 is merely exemplary, and additional or alternative factors could be included as desired. Such factors may include conductance conditions within the root canal 12 (wet/dry conditions), measured impedance, patient age and gender, apical foramen and/or canal size, as well as virtually any other recordable parameter affecting determination probe depth.

In any case, the controller 20 may determine from where to retrieve the appropriate distance value 61 after first locating a database field 52 matching the detected capacitance of the system 10. The first database field 52 may in turn link to a second field 57 in the same or another memory source that is associated with the resistance level detected from the incoming signal. Accordingly, this second field 57 may link to a third field 61 that corresponds to the distance of the probe 16 from the apex 15. In this manner, the distance value 61 ultimately retrieved from the database 50 may be derived from both measured capacitance and resistance parameters and may serve to more accurately determine root canal depth.

Data fields 59–62, which contain the determined distance values, may logically link or be otherwise correlated to a display option 48 or other indicator. In one embodiment, the exemplary display option 48 may link to programming configured to initiate a numerical digital readout, such as text or a numerical ratio, a light device, such as light emitting diode (LED) activation, and/or color and sound signals fashioned to apprize the user of probe position status.

The digital storage of the values and measurements within the database 50/lookup table 40 makes them easy to access and update, further allowing for efficient processing times. The independence of the tabled data from the algorithms required by prior art systems allows for the inclusion of data that is uniquely tailored to an application and/or clinical results. For instance, distance values established for a particular individual, or type of individual, may be entered by hand or downloaded from a file. The distance values 59–62 may subsequently be stored within memory and accessed as appropriate. Such versatility may ultimately translate into more accurate outputs. That is, the information used to populate the exemplary table, free from the constraints of conventional algorithms, may comprise experimentally verified data, not merely a calculated approximation. Such data may further account for equipment and/or patient conditions that elude conventional algorithms.

Features of the present invention further mitigate concerns regarding fluid conductivity (wet/dry conditions) in the canal 12, size aberrations, and other environmental conditions because they are accounted for in the stored data. Moreover, the stored data may be readily updated and augmented to account for patient conditions such as age, sex, radial lucency and other specific health conditions and trends.

One of skill in the art should appreciate that an embodiment of the present invention may rely on multiple such tables as shown in FIG. 3 and as described herein to arrive at an accurate distance value. One of more such tables may be easily updated and requires relatively little storage and processing capacity. In this manner, the present invention capitalizes on advances made in the fields of memory and processing to ensure the most accurate apical readings.

Such readings may be presented to the doctor via a suitable display 24 in communication with the controller 20. An exemplary display 24 is shown in FIG. 4. The display 24 includes a digital readout 64 and a graphical, stepped pie chart 63 configured to communicate a distance or relative position of the probe 16 in an easily digestible format.

According to one configuration consistent with the principles of the present invention, an exemplary display 24 may numerically present decreasing distance values as the probe 16 continues down the canal 12. At the same time the distance values are displayed, the smallest bar on the chart 63 in the middle of the display 24 may become "filled." As the probe 16 advances, the bars of the chart 63 may sequentially activate. Other suitable displays 24 may include a monitor, television, microscope, vibrating cuff, and/or auditory alarm, for example. For purposes of the invention, a suitable display 24 may comprise any device configured to communicate a sense of the relative position of the probe 16.

Figure 6:
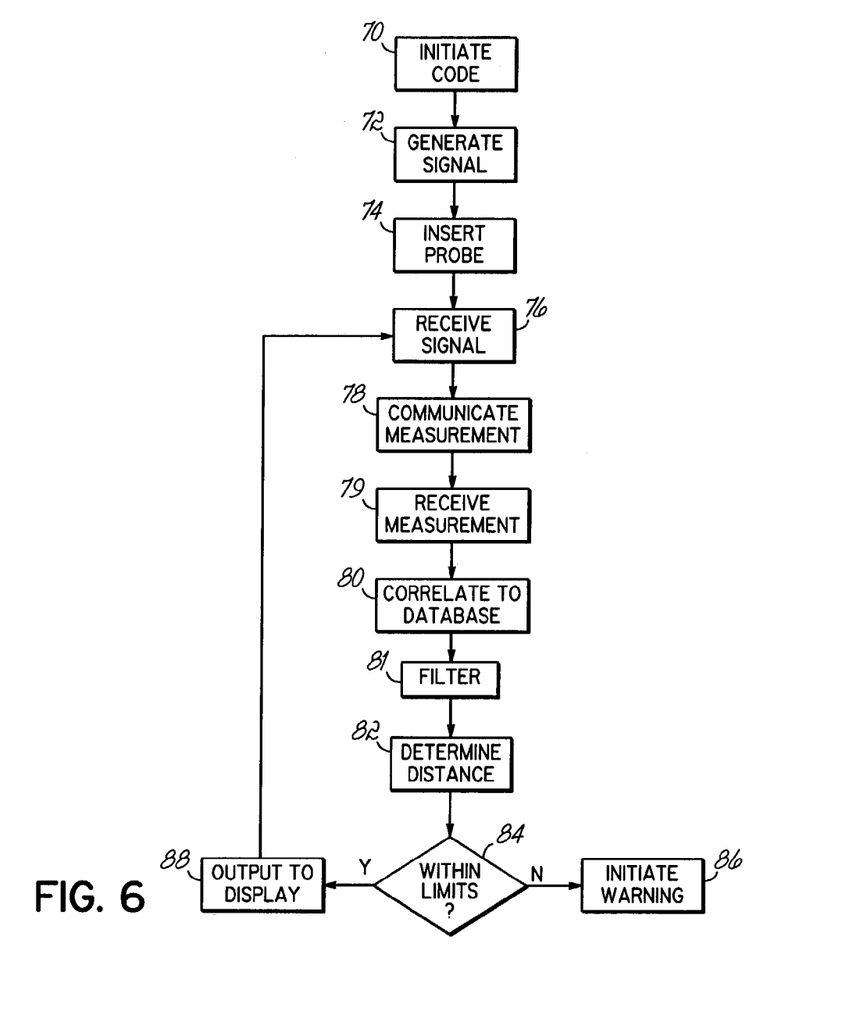
FIG. 6 is a flowchart outlining method steps of another embodiment also suited for execution within the endodontic system of FIG. 1.

The flowchart of FIG. 6 illustrates sequenced method steps suited for implementation within the hardware environment of FIG. 1. At block 70, a user may initiate or activate the apex locator system 10. Such initiation may require the user to turn on a switch or depress a button. The probe 16, electrode 18 or other detection circuit component may generate and transmit a signal at block 72. An exemplary probe 16 may include a long metal wire or a rasp. A suitable signal may be continuous and/or of a known value. The signal may convey multiple ratios, and account for different parameters, such as impedance and resistance.

A doctor may begin to insert the probe 16 into the canal 12 at block 74. Of note, the probe 16 may be inserted at any point prior to block 74 and such action is only discussed at this juncture for exemplary purposes. As discussed above, insertion of the probe 16 in an embodiment with no physical hardware may be accomplished via propagation of directed light or other electromagnetic waves. An electrode 18 or probe 16, depending upon the application configuration, may receive the signal and transmit it to the controller 20 at block 78. Such transmission may be accomplished via cable or wireless transmission, and may additionally include analog-to-digital or other format conversions.

The controller 20 may receive the transmission at block 79 and correlate the value conveyed within to a database at block 80. For instance, the controller 20 may link a field of the database corresponding to an impedance value embedded within the signal to a distance value stored within the database 22. At block 81, the program code of the controller 20 may optionally filter retrieved data. Such filtering processes may include verification of the data by reference to trends derived from the data or another data set. The verification may include assignment of confidence levels to the data for reference by a user as is known in the art.

Continuing with the processes of FIG. 6, the controller 20 may conduct an initial evaluation at blocks 82-86. Such an evaluation may involve an initial determination of the correlated distance value at block 82. More specifically, the controller 20 may determine at block 84 whether the determined distance is within predefined limits, or reference values, stipulated at block 84. Such limits may be preset by the doctor or by manufacture specifications. The limits may correspond to a maximum or minimum relative distance required by an application. Where a limit is exceeded at block 84, a controller 20 may initiate a warning signal at block 86. Such a warning signal may be conveyed via the display 24, which may include a dedicated warning device, such as a buzzer or flashing light.

Conversely, where the determined distance of the locator 16 is within predefined limits at block 84, then the output of the distance value retrieved from the database 22 may be displayed to the user at block 88. For instance, a digital readout 60 of the distance may be presented to the user. Another signal may be generated at block 72, which will be used to update the display 24 at block 88. Thus, the apex locator system 10 may cycle through continuous updates to keep the doctor apprized of the locator distance faster.

For purposes of this specification, a suitable controller 20 may be configured to receive a signal and process an instruction, or routine. One of skill in the art will appreciate that post processing of data retrieved from memory may further be accomplished by an exemplary controller 20 without straying from underlying principles of the present invention. Thus, embodiments of the invention can augment and compliment algorithms having utility in certain applications.

In general, the routines executed by the controller 20 to implement the above discussed embodiments of the invention, whether implemented as part of normal apex system program execution or a specific application, component, program, object, module or sequence of instructions are referred to herein as "commands," "programs" or "program code." Furthermore, command/program code may be interpreted as comprising multiple, distinct functions or algorithms used throughout an apex locating program sequence or operation. The commands typically comprise one or more instructions that are resident at various times in various memory and storage devices. When a command is read and executed by the controller 20 or other processor, the command causes a component of the apex locating system 10 to execute steps or elements embodying the various aspects of the invention.

Furthermore, while the invention has been described in the context of apex locators and supporting systems, those skilled in the art will appreciate that various embodiments of the invention are capable of being distributed as a program product in a variety of forms, and that the invention applies equally regardless of the particular type of signal bearing media used to actually carry out the distribution. Examples of signal bearing media include, but are not limited to recordable type media such as volatile and non-volatile memory devices, floppy and other removable discs 11, hard disc drives, opticals (e.g., CD-ROM's, DVD's, etc.), among others, and transmission type media such as digital and analog communication links.

In addition, various programs described above may be identified based upon the application for which they are implemented in a specific embodiment of the invention. However, it should be appreciated that any particular program nomenclature is used merely for convenience, and thus the invention should not be limited to use solely in any specific application identified and/or implied by such nomenclature. Moreover, those skilled in the art will recognize that the exemplary environments illustrated in FIGS. 1 and 2 are not intended to limit the present invention. Indeed, those skilled in the art will recognize that other alternative hardware and/or software environments may be used without departing from the scope of the invention.

While the exemplary sequence of steps shown in FIG. 6 may have particular utility in certain contexts, it should be understood that the order of such steps may be rearranged and/or modified to suit different system requirements. Moreover, those skilled in the art will recognize that the exemplary environments illustrated in FIGS. 1 and 3–6 are not intended to limit the present invention. Indeed, those skilled in the art will recognize that other alternative hardware and/or software environments may be used without departing from the scope of the invention.

Similarly, while the present invention has been illustrated by a description of various embodiments and while these embodiments have been described in considerable detail, it is not the intention of the applicants to restrict or in any way limit the scope of the appended claims to such detail. Additional advantages and modifications will readily appear to those skilled in the art. Similarly, the embodiments of the present invention can enhance operation of conventional. Thus, the invention in its broader aspects is therefore not limited to the specific details, representative apparatus and method, and illustrative example shown and described.

Accordingly, departures may be made from such details without departing from the spirit or scope of applicant's general inventive concept.

What is claimed is:

1. A method for determining a depth of a root canal, comprising:
   generating an electrical signal as a function of a probe's location within a tooth cavity, wherein the generated electrical signal comprises multiple frequencies;
   measuring the electrical signal with a detection circuit; and
   correlating the measured electrical signal to a distance value stored within a database containing a plurality of distance values and a plurality of electrical signal measurements, wherein each electrical signal measurement of the plurality of electrical signal measurements associates with a respective distance value of the plurality of distance values.

2. The method of claim 1, further comprising outputting the distance value to a display.

3. The method of claim 2, further comprising comparing the outputted distance value to a reference value.

4. The method of claim 3, further comprising initiating a warning sequence in response to the comparison.

5. The method of claim 1, wherein generating the electrical signal further includes generating the electrical signal as a function of at least one parameter selected from a group consisting of: a resistance measurement, an impedance measurement, root morphology, a capacitance measurement, probe dimensions, probe material, a size of the tooth cavity, an age of a patient, a sex of the patient, a particular health condition of the patient, fluid conductivity, a frequency of the electrical signal, a pulse width of the electrical signal and a distance traveled by the probe.

6. The method of claim 2, wherein outputting the distance value to the display further includes initiating a display having at least one attribute selected from a group consisting of: a numerical readout, a graphical readout, an LED, a monitor, a vibrating device and an audio cue.

7. The method of claim 1, wherein correlating the electrical signal measurement further includes associating the electrical signal measurement with at least one parameter stored in the database and selected from a group consisting of: a resistance measurement, an impedance measurement, a capacitance measurement, root morphology, a size of the probe, a size of the tooth cavity, an age of a patient, a sex of the patient, a health condition of the patient, fluid conductivity, a signal frequency, a pulse width of the electrical signal and a distance traveled by the probe.

8. The method of claim 1, further comprising inserting the probe into the tooth cavity.

9. The method of claim 1, further comprising receiving the electrical signal within the detection circuit.

10. The method of claim 1, further comprising communicating the electrical signal measurement to the controller.

11. The method of claim 10, wherein communicating the electrical signal measurement to the controller further comprises using a wireless connection.

12. The method of claim 10, wherein communicating the electrical signal measurement to the controller further comprises converting the electrical signal measurement to a digital format.

13. The method of claim 1, wherein generating the electrical signal further comprises generating the electrical signal as a function of at least two signal measurements selected from among a group consisting of: a resistance measurement, an impedance measurement and a capacitance measurement.

14. The method of claim 1, further comprising updating the database.

15. A method for determining a depth of a root canal, comprising:
   generating an electrical signal as a function of a combination of a plurality of signal measurements, wherein the generated electrical signal comprises multiple frequencies;
   detecting a plurality of signal measurements with a detection circuit; and
   correlating the signal measurements to a distance value stored within a database containing a plurality of distance values, wherein each distance value of the plurality of distance values associates with at least one signal measurement.

16. The method of claim 15, further comprising outputting the distance value to a display.

17. The method of claim 15, wherein generating the electrical signal further comprises generating the electrical signal as a function of at least two signal measurements selected from among a group consisting of: a resistance measurement, an impedance measurement and a capacitance measurement.

18. The method of claim 15, further comprising correlating the electrical signal measurements to at least one operating factor selected from a group consisting of: probe size, probe material, cavity size, patient age, patient sex, a health condition of the patient, fluid conductivity, frequency of the electrical signal, a pulse width of the electrical signal and a distance traveled by the probe.

19. The method of claim 1, wherein generating the electrical signal further comprises generating the electrical signal as a function of at least one of a resistance measurement and a capacitance measurement.

20. The method of claim 15, wherein generating the electrical signal further comprises generating the electrical signal as a function of at least of a resistance measurement and a capacitance measurement.

* * * * *